United States Patent [19]

Kampmann et al.

[11] Patent Number: 5,433,831
[45] Date of Patent: Jul. 18, 1995

[54] PROCESS FOR THE PREPARATION OF DICHLOROACETYL CHLORIDE

[75] Inventors: Detlef Kampmann, Gersthofen; Walter Freyer, Stadtbergen; Karl Bayer, Langweid-Stetten, all of Germany

[73] Assignee: Hoechst Aktiengesellschaft, Frankfurt, Germany

[21] Appl. No.: 234,390

[22] Filed: Apr. 28, 1994

[30] Foreign Application Priority Data

May 1, 1993 [DE] Germany .......... 43 14 381.4

[51] Int. Cl.$^6$ .................................. C07C 51/00
[52] U.S. Cl. ................ 204/157.6; 204/157.89; 562/860
[58] Field of Search ............ 204/157.6, 157.89; 562/860

[56] References Cited

U.S. PATENT DOCUMENTS

| | | | |
|---|---|---|---|
| 2,292,129 | 8/1942 | Kirkbride | 204/157.89 |
| 3,630,867 | 12/1971 | Petz | 204/157.89 |
| 3,884,785 | 5/1975 | Hoelle | 204/157.89 |
| 4,007,224 | 2/1977 | Pitt | 260/544 |
| 5,030,753 | 7/1991 | Freyer | 562/860 |

FOREIGN PATENT DOCUMENTS

| | | |
|---|---|---|
| 0422520 | 4/1991 | European Pat. Off. . |
| 94106474 | 7/1994 | European Pat. Off. . |
| 1530398 | 5/1968 | France . |
| 2050562 | 4/1972 | Germany . |
| 1618370 | 1/1973 | Germany . |
| 0048435 | 3/1984 | Japan . |
| 0051352 | 3/1988 | Japan . |

*Primary Examiner*—John Niebling
*Assistant Examiner*—C. Delacroix-Muirheid
*Attorney, Agent, or Firm*—Connolly and Hutz

[57] ABSTRACT

The invention relates to a process for the preparation of dichloroacetyl chloride by oxidation of trichloroethylene under pressure and at elevated temperature in the presence of a certain secondary aliphatic or cycloaliphatic amine of the formula $HNR^1R^2$ in which $R^1$ and $R^2$ are identical or different and are an alkyl radical having 1 to 10 carbon atoms, where at least one of the radicals $R^1$ and $R^2$ has a tertiary structure, or $R^1$ and $R^2$ together with the nitrogen atom form a 5- to 10-membered ring, where at least one of the carbon atoms adjacent to the nitrogen is a tertiary carbon atom. Good yields of the acid chloride and low trichloroethylene oxide contents are obtained in one process step.

17 Claims, 1 Drawing Sheet

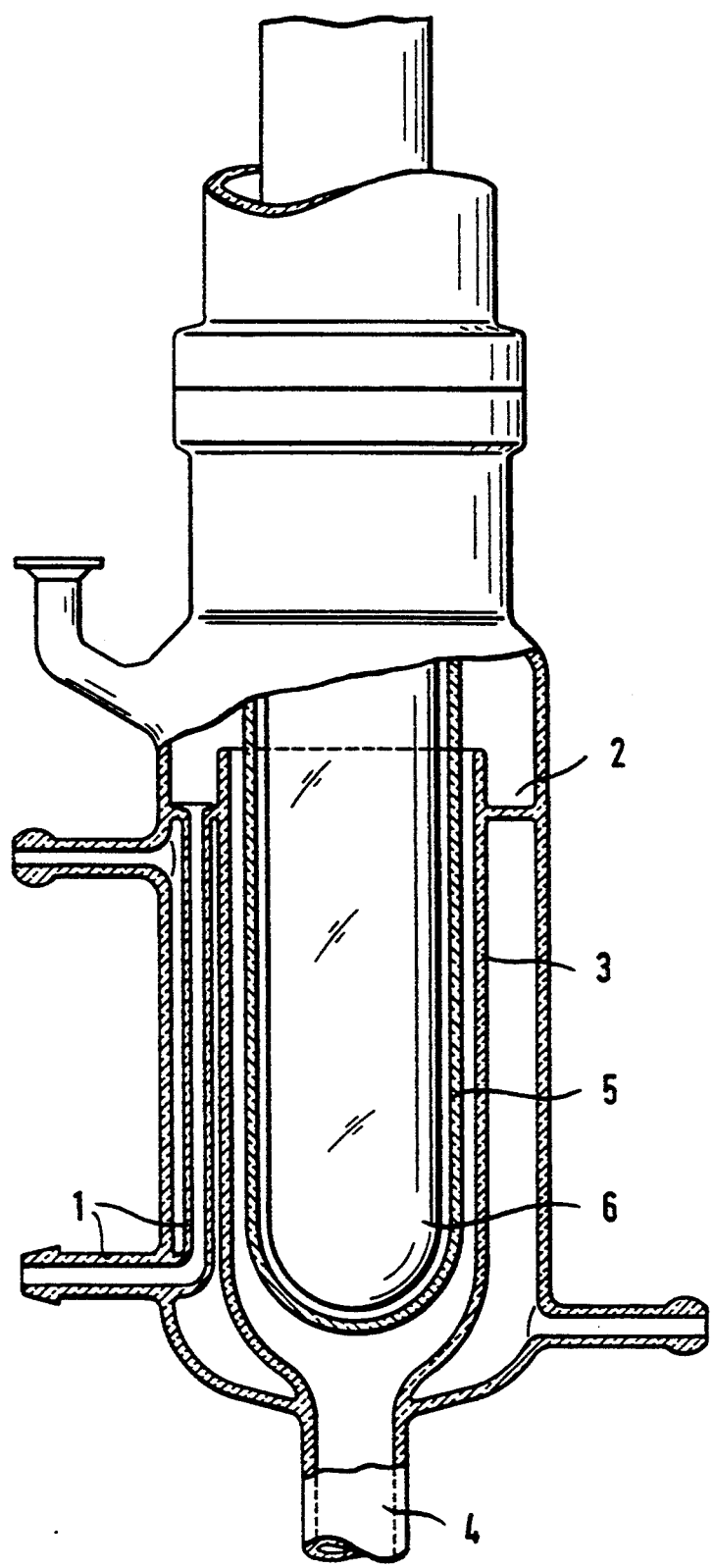

PROCESS FOR THE PREPARATION OF DICHLOROACETYL CHLORIDE

DESCRIPTION

The invention relates to a process for the preparation of dichloroacetyl chloride by oxidation of trichloroethylene under pressure and at elevated temperature, in which good yields of the acid chloride and low trichloroethylene oxide contents are obtained in one process step.

It is known that dichloroacetyl chloride is prepared by the action of oxygen or oxygen-containing gases, such as, for example, air, on trichloroethylene. This oxidation, which is conventionally carried out at a temperature between room temperature and 200° C. and without pressure or under pressure and which is initiated by free-radical initiators or irradiation, results in approximately identical amounts of dichloroacetyl chloride and trichloroethylene oxide, besides traces of high-boiling by-products and gases, such as, for example, hydrogen chloride, carbon monoxide and phosgene.

The rearrangement reaction of trichloroethylene oxide (epoxide), which is formed as an intermediate, to the acid chloride can be accelerated by adding nitrogen-containing bases (cf. U.S. Pat. Nos. 4,007,224, 3,884,785, 3,509,210).

The disadvantage of most of the known processes is their vey long reaction time, the rule being 30 to 90 hours until the reaction is complete (cf. U.S. Pat. No. 3,884,785, C.A. 109 (1988) 16987v, C.A. 101 (1984) 9093u).

Due to the long reaction time, a base-catalyzed rearrangement of the epoxide can be effected in a virtually quantitative fashion, resulting in epoxide concentrations of <3%, which are to be considered as uncritical.

A process is known for the preparation of dichloroacetyl chloride, in which the synthesis is carried out in a falling film UV reactor under pressure and at elevated temperature, increased reaction rates being achieved (cf. U.S. Pat. No. 5,030,753). However, the increased reaction rate is accompanied by a marked increase in epoxide concentration in the end product (approximately 7%). Comparison experiments showed that epoxide concentrations of as high as 15-25% can be observed in the course of the reaction. Increasing the concentration of catalyst also resulted in no improvement whatsoever. Due to the high epoxide content, handling such reaction mixtures is not without its problems.

It was therefore an object to find a process for the preparation of dichloroacetyl chloride which allows low epoxide concentrations to be achieved, despite high reaction rates.

The object is achieved by carrying out the synthesis in the presence of certain nitrogen-containing bases.

The invention therefore relates to a process for the preparation of dichloroacetyl chloride by reaction of trichloroethylene with oxygen in the liquid phase and with irradiation with short-wave light in the presence of a nitrogen-containing base, which comprises the nitrogen-containing base being a secondary aliphatic or cycloaliphatic amine of the formula $HNR^1R^2$ in which $R^1$ and $R^2$ are identical or different and are an alkyl radical having 1 to 10 carbon atoms, where at least one of the radicals $R^1$ and $R^1$ has a tertiary structure, or $R^1$ and $R^2$ together with the nitrogen atom form a 5- to 10-membered ring which can be substituted by one or more alkyl groups, where at least one of the carbon atoms adjacent to the nitrogen is a tertiary carbon atom, the nitrogen-containing base being employed in an amount of 0.001 to 0.1% by weight based on trichloroethylene.

In the process according to the invention, trichloroethylene is converted into dichloroacetyl chloride by oxidation in the liquid or gaseous phase with irradiation with short-wave light and in the presence of a nitrogen-containing base.

The reaction is carried out at a temperature of 50° to 140° C., preferably 65° to 120° C., in particular 70° to 100° C. The pressure is 0.01 to 2.0 MPa, preferably 0.03 to 1.0 MPa, particularly preferably 0.05 to 0.5 MPa.

The nitrogen-containing base employed is a secondary aliphatic or cycloaliphatic amine of the formula $HNR^1R^2$. $R^1$ and $R^2$ are identical or different and are an alkyl radical having 1 to 10 carbon atoms, preferably 3 to 8 carbon atoms, where at least one of the radicals $R^1$ and $R^2$ should have a tertiary structure, or $R^1$ and $R^2$ together with the nitrogen atom form a 5- to 10-membered, preferably 6- to 8-membered, ring which can be substituted by one or more alkyl groups, preferably methyl groups, where at least one of the carbon atoms adjacent to the nitrogen is a tertiary carbon atom.

Suitable amines are N-methyl-t-butylamine, N-ethyl-t-butylamine, N-propyl-t-butylamine, N-isopropyl-t-butylamine, N-butyl-t-butylamine, N-isobutyl-t-butylamine, N-2-methylbutyl-t-butylamine, N-3-methylbutyl-t-butylamine, N-2,3-dimethylbutyl-t-butylamine, N-pentyl-t-butylamine, N-2-ethylbutyl-t-butylamine, N-2-ethyl-hexyl-t-butylamine, 2,2,6,6-tetramethylpiperidine, 2,2,6,6-tetramethylpiperidone, 4-hydroxy-2,2,6,6-tetramethylpiperidine, preferably N-isopropyl-t-butylamine, N-isobutyl-t-butylamine, N-2-methylbutyl-t-butylamine, N-2,3-dimethylbutyl-t-butylamine, N-2-ethylbutyl-t-butylamine, N-2-ethylhexyl-t-butylamine, 2,2,6,6-tetramethylpiperidine, 2,2,6,6-tetramethylpiperidone, 4-hydroxy-2,2,6,6-tetramethylpiperidine, particularly preferably N-2-methylbutyl-t-butylamine, N-3-methylbutyl-t-butylamine, N-2,3-dimethylbutyl-t-butylamine and 2,2,6,6-tetramethylpiperidine.

It has emerged that secondary amines which have highly screened nitrogen atoms retain their catalytic property for the rearrangement reaction of trichloroethylene oxide to dichloroacetyl chloride to the full extent, even when the partial pressure of oxygen is increased. This is particularly surprising since secondary amines of this structural class are frequently used as light stabilizers for polymers (free-radical scavengers), which is why they would rather be expected to have a negative effect on the reaction in question.

The amine is employed in an amount of 0.001 to 0.1, preferably 0.003 to 0.5, % by weight based on trichloroethylene employed. This corresponds to a few ppm based on the nitrogen. The amount depends on the reaction conditions and is within a range of 1 to 100 ppm, preferably 3 to 50 ppm, in particular 5 to 30 ppm, of nitrogen.

The reaction of trichloroethylene with oxygen is effected in the presence of this amine and is initiated by free-radical initiators. In the preferred procedure, this is effected by irradiation with short-wave light, for example UV light of an Hg high-pressure burner.

An excess of oxygen is continuously fed to the reaction system, a molar ratio of 1.1:1 to 5:1, preferably 1.2:1 to 4:1 and, in particular, 1.5:1 to 3.5:1 being sufficient.

Unreacted oxygen is continuously removed together with gaseous by-products in such a way that the pressure of the system remains constant. The waste gas is subjected to alkaline waste-gas purification in order to absorb by-products such as, for example, phosgene and HCl.

The process according to the invention can be carried out in a falling film reactor and also in a bubble-cap column reactor, the batchwise or continuous procedure being possible.

With regard to a good overall yield and high reaction rates, a partial reaction of 40 to 70% is preferred. Unreacted trichloroethylene can be removed without problems by distillation and can be recirculated to the reaction system.

COMPARISON EXPERIMENT A

The experiments were carried out in a falling film photoreactor as described by Professor de Meijere. The most important characteristics of the reactor are shown in the figure. The reaction mixture enters the reactor via the tube (1), fills the circular trough (2), and flows through the lower tube section (4) on the inside of the cylindrical tube (3) in the form of a thin film to the pump of the circuit (not shown).

The reactor can also be used in the form of a bubble-cap column reactor. In this case, the reactor is flooded up to the circular trough.

A UV light source (6) equipped with cooling jacket is arranged in the protective tube (5). Such photoreactors are available from specialist firms.

The reactor was equipped with a storage vessel (variable from 250 cm$^3$ to 2,000 cm$^3$) for the mixture used in the circuit, a dropping funnel for the starting material and a multiple coil condenser with a heat exchanger arranged downstream for cooling the waste gas. A reduction valve and a pressure gauge, which were used for adjusting the system pressure, were integrated in the waste-gas pipe, which opened into an NaOH scrubber.

The UV light source used was a mercury high-pressure burner of the type TQ 150. The cooling jacket of the burner was cooled using water. The oxygen was metered continuously into the reactor via a fritted bottom, and the quantity used was determined by means of a ®Rotameter.

For the experiments, the trichloroethylene and the amine were each introduced into the apparatus, the circulating pump was switched on, and the apparatus was heated using a thermostat. The multiple coil condenser and the heat exchanger were held at constant temperature (about −20° C.) by means of a cryostat.

After a suitable starting-up time of the UV burner, the oxygen was passed in continuously at a constant rate. The stream of waste gas was adjusted by means of the reduction valve in such a way that it was possible to keep constant the preselected pressure.

1,000 g of trichloroethylene were treated with 82 mg of pyridine (=14.5 ppm of N) and oxidized at 75° C. in a bubble-cap column operation at an $O_2$ overpressure of 0.03 MPa. The amount of gas used was 60 dm$^3$/h. The reaction was observed over a period of 4 hours, and the analyses by gas chromatography are shown in Table 1.

After 4 hours, the conversion of trichloroethylene to dichloroacetyl chloride was 87.8% (=0.88 kg) with a selectivity of 77.4%.

TABLE 1

| Reaction time [h] | 1 | 2 | 3 | 4 |
|---|---|---|---|---|
| Trichloroethylene [%] | 72.5 | 48.1 | 26.4 | 12.2 |
| Dichloroacetyl chloride [%] | 23.1 | 40.3 | 58.0 | 68.0 |
| Trichloroethylene oxide [%] | 2.9 | 9.2 | 13.1 | 16.4 |

COMPARISON EXPERIMENT B

As in Comparison Experiment A, 1,000 g of trichloroethylene were reacted with 82 mg of pyridine at 75° C., an $O_2$ overpressure of 0.05 MPa having been set.

The course of the reaction can be found in Table 2.

After 4 hours, the conversion of trichloroethylene was 89% (=0.89 kg), with a selectivity of 68.5% based on dichloroacetyl chloride.

TABLE 2

| Reaction time [h] | 1 | 2 | 3 | 4 |
|---|---|---|---|---|
| Trichloroethylene [%] | 73.6 | 45.9 | 25.6 | 11.0 |
| Dichloroacetyl chloride [%] | 22.2 | 37.0 | 50.7 | 61.0 |
| Trichloroethylene oxide [%] | 2.6 | 13.9 | 20.1 | 24.6 |

COMPARISON EXPERIMENT C

As in Comparison Experiment B, 1,000 g of trichloroethylene were reacted at 75° C., and an $O_2$ overpressure of 0.05 MPa. The amount of rearrangement catalyst was doubled (164 mg of pyridine).

The course of the reaction is shown in Table 3.

After 4 hours, the conversion to dichloroacetyl chloride was 90.6% (=0.91 kg) with a selectivity of 76%.

TABLE 3

| Reaction time [h] | 1 | 2 | 3 | 4 |
|---|---|---|---|---|
| Trichloroethylene [%] | 75.1 | 46.7 | 24.5 | 9.4 |
| Dichloroacetyl chloride [%] | 21.9 | 42.3 | 59.0 | 68.9 |
| Trichloroethylene oxide [%] | 1.4 | 7.8 | 13.7 | 18.5 |

COMPARISON EXPERIMENT D

As in Comparison Experiment C, 1,000 g of trichloroethylene were reacted with 164 mg of pyridine and an $O_2$ overpressure of 0.05 MPa. The reaction temperature was raised to 80° C.

After 4 hours, the conversion of trichloroethylene was 88.2% (=0.88 kg) with a selectivity of 66.9% based on dichloroacetyl chloride.

The course of the reaction was as follows (Table 4).

TABLE 4

| Reaction time [h] | 1 | 2 | 3 | 4 |
|---|---|---|---|---|
| Trichloroethylene [%] | 72.3 | 47.8 | 26.1 | 11.8 |
| Dichloroacetyl chloride [%] | 23.1 | 40.2 | 50.9 | 59.0 |
| Trichloroethylene oxide [%] | 2.8 | 9.5 | 20.1 | 26.0 |

COMPARISON EXPERIMENT E

As in Comparison Experiment A, 1,200 g of trichloroethylene were reacted at 80° C., and an $O_2$ overpressure of 0.075 MPa. The rearrangement catalyst employed was dimethylformamide (95 mg=15.2 ppm of N).

The course of the reaction can be seen in Table 5.

After 4 hours, the conversion of trichloroethylene was 90.1% (=1.08 kg) with a selectivity of 75.6% based on dichloroacetyl chloride.

TABLE 5

| Reaction time [h] | 1 | 2 | 3 | 4 |
|---|---|---|---|---|
| Trichloroethylene [%] | 60.4 | 36.8 | 20.2 | 9.9 |
| Dichloroacetyl chloride [%] | 26.8 | 48.0 | 62.3 | 68.1 |
| Trichloroethylene oxide [%] | 9.0 | 12.3 | 14.3 | 19.1 |

COMPARISON EXPERIMENT F

Analogously to Experiment 5, 1,400 g of trichloroethylene were reacted at 80° C., and an $O_2$ overpressure of 0.075 MPa. The rearrangement catalyst used was triethanolamine (130 mg=9 ppm of N).

The course of the reaction is shown in Table 6.

After 4 hours, 81.9% (=1.15 kg) of the trichloroethylene had been reacted with a selectivity of 69.5%.

TABLE 6

| Reaction time [h] | 1 | 2 | 3 | 4 |
|---|---|---|---|---|
| Trichloroethylene [%] | 79.7 | 57.0 | 38.2 | 18.1 |
| Dichloroacetyl chloride [%] | 14.8 | 29.4 | 42.0 | 56.9 |
| Trichloroethylene oxide [%] | 4.1 | 10.2 | 16.6 | 21.8 |

EXAMPLE 1

As in Comparison Experiment A, 1,200 g of trichloroethylene were reacted at 80° C., and an $O_2$ overpressure of 0.075 MPa. The rearrangement catalyst used was 2,2,6,6-tetramethylpiperidine (83 mg=7 ppm of N).

The result is shown in Table 7.

After a reaction time of 4 hours, 90.1% (=1.08 kg) of trichloroethylene had been reacted. The selectivity based on the end product was 94.6%.

TABLE 7

| Reaction time [h] | 1 | 2 | 3 | 4 |
|---|---|---|---|---|
| Trichloroethylene [%] | 66.1 | 38.8 | 20.4 | 9.9 |
| Dichloroacetyl chloride [%] | 28.6 | 55.5 | 74.6 | 85.3 |
| Trichloroethylene oxide [%] | 3.4 | 3.1 | 2.2 | 1.8 |

EXAMPLE 2

As in Example 1, 1,400 g of trichloroethylene were reacted in a falling film at 80° C., and an $O_2$ overpressure of 0.075 MPa. 99.6 mg (=7 ppm of N) of 2,2,6,6-tetramethylpiperidine were used.

The course of the experiment is shown in Table 8. A trichloroethylene conversion of 80.32% (=1.12 kg) was achieved with a selectivity of 93.0%.

TABLE 8

| Reaction time [h] | 1 | 2 | 3 | 4 |
|---|---|---|---|---|
| Trichloroethylene [%] | 80.0 | 60.2 | 33.4 | 19.7 |
| Dichloroacetyl chloride [%] | 15.3 | 34.2 | 60.5 | 74.7 |
| Trichloroethylene oxide [%] | 3.2 | 3.1 | 3.0 | 2.4 |

EXAMPLE 3

As in Example 2, 1,400 g of trichloroethylene were reacted in a falling film at 80° C., and an $O_2$ overpressure of 0.075 MPa. 216 mg (=15 ppm of N) of 2,2,6,6-tetramethylpiperidine were used.

The course of the reaction is shown in Table 9. After 4 hours, the conversion of trichloroethylene was 81.4% (=1.14 kg), the selectivity being 95.5%.

TABLE 9

| Reaction time [h] | 1 | 2 | 3 | 4 |
|---|---|---|---|---|
| Trichloroethylene [%] | 77.4 | 55.7 | 35.5 | 18.6 |
| Dichloroacetyl chloride [%] | 20.7 | 40.4 | 61.5 | 77.8 |
| Trichloroethylene oxide [%] | 0.5 | 0.6 | 0.2 | 0.3 |

EXAMPLE 4

As in Example 3, 1,400 g of trichloroethylene were reacted in a falling film at 80° C., and an $O_2$ overpressure of 0.075 MPa. 96 mg (=6 ppm of N) of N-2,3-dimethyl-butyl-t-butylamine were employed as catalyst.

After 4 hours, the conversion of trichloroethylene was 82.1% (=1.15 kg), a selectivity of 94.7% having been achieved.

The course of the reaction is shown in Table 10.

TABLE 10

| Reaction time [h] | 1 | 2 | 3 | 4 |
|---|---|---|---|---|
| Trichloroethylene [%] | 77.3 | 55.0 | 34.7 | 17.9 |
| Dichloroacetyl chloride [%] | 21.0 | 42.0 | 61.7 | 77.8 |
| Trichloroethylene oxide [%] | 0.4 | 0.6 | 0.9 | 1.3 |

EXAMPLE 5

As in Example 4, 1,400 g of trichloroethylene were reacted in a falling film at 80° C., and an $O_2$ overpressure of 0.075 MPa. 104 mg (=8 ppm of N) of N-isobutyl-tertbutylamine were used as catalyst. After a reaction time of 4 hours, 82.2% (=1.15 kg), of trichloroethylene had been reacted. The selectivity was 93.4%.

The course of the reaction can be found in Table 11.

TABLE 11

| Reaction time [h] | 1 | 2 | 3 | 4 |
|---|---|---|---|---|
| Trichloroethylene [%] | 77.5 | 56.2 | 35.9 | 17.8 |
| Dichloroacetyl chloride [%] | 20.4 | 40.9 | 59.9 | 76.7 |
| Trichloroethylene oxide [%] | 0.2 | 0.5 | 1.0 | 2.0 |

EXAMPLE 6

As in Example 1, 2,000 g of trichloroethylene were reacted at 80° C., and an $O_2$ overpressure of 0.075 MPa. To carry out the rearrangement reaction, 304 mg (=15 ppm of N) of 2,2,6,6-tetramethylpiperidine were added. After 4 hours, 68.4% (=1.38 kg) of trichloroethylene had been reacted, a selectivity of 94.1% having been achieved.

The course of the reaction is shown in Table 12.

TABLE 12

| Reaction time [h] | 1 | 2 | 3 | 4 |
|---|---|---|---|---|
| Trichloroethylene [%] | 80.6 | 63.4 | 46.8 | 31.6 |
| Dichloroacetyl chloride [%] | 16.1 | 33.3 | 48.5 | 64.4 |
| Trichloroethylene oxide [%] | 1.0 | 1.0 | 1.8 | 0.9 |

We claim:

1. A process for preparing dichloroacetyl chloride comprising the step of reacting trichloroethylene with oxygen in a reaction system having a liquid phase while irradiating with short-wave light in the presence of a nitrogen containing base, wherein the nitrogen-containing base comprises a secondary aliphatic or cycloaliphatic amine of a formula $HNR^1R^2$ in which $R^1$ and $R^2$ are identical or different and are an alkyl radical having 1 to 10 carbon atoms, where at least one of the radicals $R^1$ and $R^2$ has a tertiary structure, or $R^1$ and $R^2$ together with the nitrogen atom form a 5- or 10-membered ring which can be substituted by one or more alkyl groups, where at least one of the carbon atoms adjacent to the nitrogen atom is a tertiary carbon atom, where the nitrogen-containing base is employed in an amount of from 0.001 to 0.1% by weight base on trichloroethylene, and where the reaction is carried out in one process step.

2. The process as claimed in claim 1, wherein the nitrogen-containing base is selected from the group consisting of N-isopropyl-t-butylamine, N-isobutyl-t-butylamine, N-2-methylbutyl-t-butylamine, N-2,3-dimethylbutyl-t-butylamine, N-2-ethylbutyl-t-butylamine, N-2-ethylhexyl-t-butylamine, 2,2,6,6-tetramethylpiperidine and 4-hydroxy-2,2,6,6-tetramethylpiperidine.

3. The process as claimed in claim 1, wherein the nitrogen-containing base is selected from the group consisting of is N-2-methylbutyl-t-butylamine, N-3-methylbutyl-t-butylamine, N-2,3-dimethylbutyl-t-butylamine and 2,2,6,6tetramethylpiperidine.

4. A process as claimed in claim 1, wherein the reaction is carried out at a temperature of from 50° to 140° C.

5. A process as claimed in claim 1, wherein the reaction is carried out at a temperature of from 65° to 120° C.

6. A process as claimed in claim 1, wherein the reaction is carried out at a temperature of from 70° to 100° C.

7. A process as claimed in claim 1, wherein the reaction is carried out under a pressure of from 0.01 to 2.00 MPa.

8. A process as claimed in claim 1, wherein the reaction is carried out at a pressure of from 0.03 to 1.0 MPa.

9. A process as claimed in claim 1, wherein the reaction is carried out under a pressure of from 0.05 to 0.5 MPa.

10. A process as claimed in claim 1, wherein the nitrogen-containing base is a secondary aliphatic or cycloaliphatic amine of the formula $HNR^1R^2$, wherein $R^1$ and $R^2$ are identical or different and are an alkyl radical having 3 to 8 carbon atoms.

11. A process as claimed in claim 1, wherein the amine is employed in an amount of from 0.003 to 0.5% by weight based on trichloroethylene.

12. A process as claimed in claim 1, wherein an excess of oxygen is continuously fed to the reaction system.

13. A process as claimed in claim 12, wherein the oxygen is fed to the reaction system in a molar ratio of 1.1:1 to 5:1.

14. A process as claimed in claim 12, wherein the oxygen which is fed to the reaction system is fed in a molar ratio of from 1.2:1 to 4:1.

15. A process as claimed in claim 12, wherein the oxygen which is fed to the reaction system is fed in a molar ratio of from 1.5:1 to 3.5:1.

16. A process for preparing dichloroacetyl chloride comprising the step of reacting trichloroethylene with oxygen in a reaction, system having a liquid phase while irradiating with short-wave light in the presence of a nitrogen containing base, wherein the nitrogen-containing base comprises a secondary aliphatic or cycloaliphatic amine of a formula $HNR^1R^2$ in which $R^1$ and $R^2$ are identical or different and are an alkyl radical having 1 to 10 carbon atoms, where at least one of the radicals $R^1$ and $R^2$ has a tertiary structure, or $R^1$ and $R^2$ together with the nitrogen atom form a 5- or 10-membered ring which can be substituted by one or more alkyl groups, where at least one of the carbon atoms adjacent to the nitrogen atom is a tertiary carbon atom, where the nitrogen-containing base is employed in an amount of from 0.001 to 0.1% by weight base on trichloroethylene, and where the reaction is carried out in one process step and the reaction is substantially completed within four hours.

17. A process as claimed in claim 1, wherein the process is substantially complete within about four hours.

* * * * *